US012584117B2

(12) United States Patent
Yu et al.

(10) Patent No.: US 12,584,117 B2
(45) Date of Patent: Mar. 24, 2026

(54) **USE OF GENE ENCODING GIBBERELLIN 3BETA-HYDROXYLASE OF *GLYCINE MAX*, GmGA3ox1**

(71) Applicant: Nanjing Agricultural University, Nanjing (CN)

(72) Inventors: Deyue Yu, Nanjing (CN); Fang Huang, Nanjing (CN); Dezhou Hu, Nanjing (CN); Hui Wang, Nanjing (CN); Zhongyi Yang, Nanjing (CN); Shaoqi Lu, Nanjing (CN); Xiao Li, Nanjing (CN)

(73) Assignee: Nanjing Agricultural University, Nanjing (CN)

( * ) Notice: Subject to any disclaimer, the term of this patent is extended or adjusted under 35 U.S.C. 154(b) by 139 days.

(21) Appl. No.: 18/031,159

(22) PCT Filed: Jul. 21, 2022

(86) PCT No.: PCT/CN2022/106929
§ 371 (c)(1),
(2) Date: Apr. 11, 2023

(87) PCT Pub. No.: WO2023/087761
PCT Pub. Date: May 25, 2023

(65) Prior Publication Data
US 2023/0313151 A1 Oct. 5, 2023

(30) Foreign Application Priority Data

Nov. 17, 2021 (CN) .......................... 202111360441.9

(51) Int. Cl.
| | |
|---|---|
| *C12N 9/02* | (2006.01) |
| *A01H 1/04* | (2006.01) |
| *A01H 5/10* | (2018.01) |
| *A01H 6/20* | (2018.01) |
| *A01H 6/54* | (2018.01) |
| *C12Q 1/6895* | (2018.01) |

(52) U.S. Cl.
CPC .......... *C12N 9/0071* (2013.01); *A01H 1/045* (2021.01); *A01H 5/10* (2013.01); *A01H 6/20* (2018.05); *A01H 6/542* (2018.05); *C12Q 1/6895* (2013.01); *C12Y 114/11015* (2013.01); *C12Q 2600/158* (2013.01)

(58) Field of Classification Search
CPC ........ C12N 9/0071; A01H 6/542; A01H 6/20; A01H 1/045; A01H 5/10; C12Q 1/6895; C12Q 2600/158; C12Y 114/11015
See application file for complete search history.

(56) References Cited

FOREIGN PATENT DOCUMENTS

CN 114277041 A 4/2022

OTHER PUBLICATIONS

Mitchum et al (2006) The Plant Journal 45, 804-818. (Year: 2006).*
Li et al (2013) Plant Growth Regul. 70:27-37 (Year: 2013).*
Shahnejat-Bushehri et al (2016) Nature plants, 2(3), 1-9. (Year: 2016).*
NCBI Reference Sequence XM_003529772.4: https://www.ncbi.nlm.nih.gov/nucleotide/XM_003529772.4?report=genbank (Year: 2018).*
NCBI Sequence Accession No. XM_028363880.1: https://www.ncbi.nlm.nih.gov/nucleotide/XM_028363880?report=genbank (Year: 2019).*
Hu et al (2022) New Phytologist 235: 502-517. (Year: 2022).*
Xue et al (2022) Int. J. Mol. Sci. 23, 1721. (Year: 2022).*
Li et al (2022) International Journal of Biological Macromolecules. 209A: 1319-1326 (Year: 2022).*
Lee et al (2013) An overview of genetic transformation of soybean. IntechOpen. (Year: 2013).*
Chen et al (2003) Molecular Breeding. 11: 287-293. (Year: 2003).*
Butel et al (2021) Nature Communications. 12:2787. (Year: 2021).*
Han et al (2011) Gene. 473: 23-25. (Year: 2011).*
NCBI Reference Sequence XM_003529772.5: https://www.ncbi.nlm.nih.gov/nuccore/XM_003529772.5/ (Year: 2024).*
NCBI Gene Record GA30X1: https://www.ncbi.nlm.nih.gov/gene/?term=gmga3ox1 (Year: 2025).*
NHGRI Genetics Glossary entry for cDNA: https://www.genome.gov/genetics-glossary/copy-DNA-cDNA (Year: 2025).*
Han, Yiqiang; Shi, Ying; Ya, Mei; Zheng, Dianfeng, Du, Jidao; Zhang, Yuxian; Feng, Naijie, "Effects of gibberellins and uniconazole on morphology, photosynthetic physiology and yield of soybean," Chinese Journal of Oil Crop Sciences), Dec. 28, 2018, pp. 820-827, vol. 40(60), China.
Predicted: Glycine soja gibberellin 3-beta-dioxygenase 1-likeGenbank: XM_028386239.1, Mar. 12, 2019 (Mar. 12, 2019).
Sun, Hao; "Biological Functional Analysis of Gibberellin Synthesis Gene MtGA3ox1 in Medicago truncatula," Chinese DoctoralDissertations Full-Text Database (Basic Sciences)), No. {0} 2021, 01, Jan. 15, 2021 (Jan. 15, 2021) pp. 1-120, China.

* cited by examiner

*Primary Examiner* — Anne Kubelik
*Assistant Examiner* — Victoria L Deleo
(74) *Attorney, Agent, or Firm* — Luedeka Neely, P.C.

(57) ABSTRACT

Provided is a use of gene encoding gibberellin 3B-hydroxylase of *G. max*, GmGA3ox1. The use of gibberellin 3β-hydroxylase gene of *G. max*, GmGA3Ox1, set forth in SEQ ID NO:1, is in genetic engineering of seed weight of *Arabidopsis thaliana* and *Glycine max*. In *A. thaliana*, overexpression of GmGA3ox1 can complement the low seed weight phenotype of an atga3ox1 mutant. In *G. max*, overexpression of the excellent haplotype of the gene can significantly improve the seed weight of *G. max*.

2 Claims, 11 Drawing Sheets

Specification includes a Sequence Listing.

GFP          Light          Merge

*35S:GmGA3ox1-GFP*

*35S:GFP*

Col-0                    atga3ox1

1#-1       1#-2       2#-1       2#-2       3#-1       3#-2

35S:GmGA3ox1/atga3ox1

B

Col-0     atga3ox1    1#         2#         3#

35S:GmGA3ox1/atga3ox1

D

E

F

G

A

B

C

D

E

F

SEQUENCE LISTING

```
Sequence total quantity: 24
SEQ ID NO: 1              moltype = DNA  length = 1137
FEATURE                   Location/Qualifiers
source                    1..1137
                          mol_type = genomic DNA
                          note = Nucleotide sequence of GmGA3ox1
                          organism = Glycine max
SEQUENCE: 1
atgccttctc tctccgaagc ctttagaggt caccccgtgt accttcatca caaacactcc   60
gacttcaact cacttcaaga actccctgac tcttactctt ggacacaacc ccatgatcac  120
catctcccaa attacccttc caacaataag accaagatct ttgtccccgt aatcgatttg  180
aaccacccaa atgctccaaa cctcataggc catgcatgca aaacatgggg tgtgttccaa  240
gtggtgaacc atgacatccc catgagcctc ttcagtgaca ttcagagggc tagtcttgcg  300
ttattctccc ttccccttca ccagaagctc aaagcagctc gctcccccga cggcgtctcc  360
ggctatggcc gcgctcgcat ctcctccttc ttccccaagc tcatgtggtc tgagtgcttc  420
acaattctcg attcccctct tgatcttttc ctcaaactct ggccacaaga ctatgctaaa  480
tactgtgata ttgtcgtgga atatgaagca gccatgaaaa agctagcagc gaaattaatg  540
tgcctcatgt tggcttccct tggaattaca aaggaagaca ctaaatgggc tgggccaaaa  600
ggagaattca atggggcttg tgcggccttg cacttgaatt cttacccgag ttgcccggat  660
ccggatcgag ccatgggtct ggccgcacac accgactcca ctctcctcac aatcctacac  720
caaaacaatg tcaatgggct tcaagttctc aaggaaggag aagggtgggt ggcagtgccg  780
ccgcttcacg gagggctcgt gattaacgtt ggcgatctgc tccacatttt gtcaaacggg  840
ttgtacccga gtgtgctcca tcgggttcgg gtgaaccgaa cccaacagcg gttctcggtt  900
gcttatctat atgggccccc agcaaacgtc caaatcagtc cacatgtcaa gttggtgggc  960
ccaacaaggc ccgctcttta tcgaccagtg acttggaacg agtaccttgg caccaaagca 1020
aacctttta ataaggctct ttcagcggtt aggctttctg cgtctattaa cggtttgttt 1080
gatataaacg aggatcagaa taacgacttt caagtgggct tcaatctaga tatttag    1137

SEQ ID NO: 2              moltype = AA  length = 378
FEATURE                   Location/Qualifiers
source                    1..378
                          mol_type = protein
                          note = GmGA3ox1 gene encoded amino acid sequence
                          organism = Glycine max
```

-continued

```
SEQUENCE: 2
MPSLSEAFRG HPVYLHHKHS DFNSLQELPD SYSWTQPHDH HLPNYPSNNK TKIFVPVIDL   60
NHPNAPNLIG HACKTWGVFQ VVNHDIPMSL FSDIQRASLA LFSLPLHQKL KAARSPDGVS  120
GYGRARISSF FPKLMWSECF TILDSPLDLF LKLWPQDYAK YCDIVVEYEA AMKKLAAKLM  180
CLMLASLGIT KEDTKWAGPK GEFNGACAAL HLNSYPSCPD PDRAMGLAAH TDSTLLTILH  240
QNNVNGLQVL KEGEGWVAVP PLHGGLVINV GDLLHILSNG LYPSVLHRVR VNRTQQRFSV  300
AYLYGPPANV QISPHVKLVG PTRPALYRPV TWNEYLGTKA NLFNKALSAV RLSASINGLF  360
DINEDQNNDF QVGFNLDI                                               378

SEQ ID NO: 3            moltype = DNA   length = 22
FEATURE                 Location/Qualifiers
source                  1..22
                        mol_type = other DNA
                        note = Primer
                        organism = synthetic construct
SEQUENCE: 3
atgccttctc tctccgaagc ct                                          22

SEQ ID NO: 4            moltype = DNA   length = 19
FEATURE                 Location/Qualifiers
source                  1..19
                        mol_type = other DNA
                        note = Primer
                        organism = synthetic construct
SEQUENCE: 4
ctaaatatct agattgaag                                              19

SEQ ID NO: 5            moltype = DNA   length = 22
FEATURE                 Location/Qualifiers
source                  1..22
                        mol_type = other DNA
                        note = Primer
                        organism = synthetic construct
SEQUENCE: 5
agtccacatg tcaagttggt gg                                          22

SEQ ID NO: 6            moltype = DNA   length = 21
FEATURE                 Location/Qualifiers
source                  1..21
                        mol_type = other DNA
                        note = Primer
                        organism = synthetic construct
SEQUENCE: 6
cggttaggct ttctgcgtct a                                           21

SEQ ID NO: 7            moltype = DNA   length = 22
FEATURE                 Location/Qualifiers
source                  1..22
                        mol_type = other DNA
                        note = Primer
                        organism = synthetic construct
SEQUENCE: 7
cctcgttcga attcgctttt tg                                          22

SEQ ID NO: 8            moltype = DNA   length = 22
FEATURE                 Location/Qualifiers
source                  1..22
                        mol_type = other DNA
                        note = Primer
                        organism = synthetic construct
SEQUENCE: 8
caactgtctt gtcacttggc at                                          22

SEQ ID NO: 9            moltype = DNA   length = 41
FEATURE                 Location/Qualifiers
source                  1..41
                        mol_type = other DNA
                        note = Primer
                        organism = synthetic construct
SEQUENCE: 9
cagctatgac catgattact cacatcgata aacgaggttt g                     41

SEQ ID NO: 10           moltype = DNA   length = 39
FEATURE                 Location/Qualifiers
source                  1..39
                        mol_type = other DNA
                        note = Primer
                        organism = synthetic construct
SEQUENCE: 10
```

-continued

```
agtgccaagc ttggctgcag attgtgttga atgcttcgg                              39

SEQ ID NO: 11            moltype = DNA   length = 39
FEATURE                  Location/Qualifiers
source                   1..39
                         mol_type = other DNA
                         note = Primer
                         organism = synthetic construct
SEQUENCE: 11
cagctatgac catgattact cacgatccca acattcgtg                              39

SEQ ID NO: 12            moltype = DNA   length = 39
FEATURE                  Location/Qualifiers
source                   1..39
                         mol_type = other DNA
                         note = Primer
                         organism = synthetic construct
SEQUENCE: 12
agtgccaagc ttggctgcag attgtgttga atgcttcgg                              39

SEQ ID NO: 13            moltype = DNA   length = 42
FEATURE                  Location/Qualifiers
source                   1..42
                         mol_type = other DNA
                         note = Primer
                         organism = synthetic construct
SEQUENCE: 13
cagctatgac catgattacc acctagtgag agagaaagaa gg                          42

SEQ ID NO: 14            moltype = DNA   length = 39
FEATURE                  Location/Qualifiers
source                   1..39
                         mol_type = other DNA
                         note = Primer
                         organism = synthetic construct
SEQUENCE: 14
agtgccaagc ttggctgcag attgtgttga atgcttcgg                              39

SEQ ID NO: 15            moltype = DNA   length = 30
FEATURE                  Location/Qualifiers
source                   1..30
                         mol_type = other DNA
                         note = Primer
                         organism = synthetic construct
SEQUENCE: 15
cctctagaat gccttctctc tccgaagcct                                        30

SEQ ID NO: 16            moltype = DNA   length = 25
FEATURE                  Location/Qualifiers
source                   1..25
                         mol_type = other DNA
                         note = Primer
                         organism = synthetic construct
SEQUENCE: 16
ccgctcgaga atatctagat tgaag                                             25

SEQ ID NO: 17            moltype = DNA   length = 42
FEATURE                  Location/Qualifiers
source                   1..42
                         mol_type = other DNA
                         note = Primer
                         organism = synthetic construct
SEQUENCE: 17
gtcgacggta tcgataagct tatgccttct ctctccgaag cc                          42

SEQ ID NO: 18            moltype = DNA   length = 45
FEATURE                  Location/Qualifiers
source                   1..45
                         mol_type = other DNA
                         note = Primer
                         organism = synthetic construct
SEQUENCE: 18
cgctctagaa ctagtggatc cctaaatatc tagattgaag cccac                       45

SEQ ID NO: 19            moltype = DNA   length = 24
FEATURE                  Location/Qualifiers
source                   1..24
                         mol_type = other DNA
                         note = Primer
```

-continued

```
                             organism = synthetic construct
SEQUENCE: 19
ggatatgttg aaactttcct ttgc                                         24

SEQ ID NO: 20          moltype = DNA   length = 20
FEATURE                Location/Qualifiers
source                 1..20
                       mol_type = other DNA
                       note = Primer
                       organism = synthetic construct
SEQUENCE: 20
atgcatgatc aatcatttac                                              20

SEQ ID NO: 21          moltype = DNA   length = 22
FEATURE                Location/Qualifiers
source                 1..22
                       mol_type = other DNA
                       note = Primer
                       organism = synthetic construct
SEQUENCE: 21
atgccttctc tctccgaagc ct                                           22

SEQ ID NO: 22          moltype = DNA   length = 20
FEATURE                Location/Qualifiers
source                 1..20
                       mol_type = other DNA
                       note = Primer
                       organism = synthetic construct
SEQUENCE: 22
aagaccggca acaggattca                                              20

SEQ ID NO: 23          moltype = DNA   length = 22
FEATURE                Location/Qualifiers
source                 1..22
                       mol_type = other DNA
                       note = Primer
                       organism = synthetic construct
SEQUENCE: 23
agtccacatg tcaagttggt gg                                           22

SEQ ID NO: 24          moltype = DNA   length = 23
FEATURE                Location/Qualifiers
source                 1..23
                       mol_type = other DNA
                       note = Primer
                       organism = synthetic construct
SEQUENCE: 24
ccggcaacag gattcaatct taa                                          23
```

USE OF GENE ENCODING GIBBERELLIN 3BETA-HYDROXYLASE OF *GLYCINE MAX*, GmGA3ox1

CROSS-REFERENCE TO RELATED APPLICATION

This patent application claims the benefit and priority of Chinese Patent Application No. 202111360441.9 filed with the China National Intellectual Property Administration on Nov. 17, 2021, and entitled "USE OF GENE ENCODING GIBBERELLIN 3β-HYDROXYLASE of *Glycine max*, GmGA3ox1", the disclosure of which is incorporated by reference herein in its entirety as part of the present application.

REFERENCE TO SEQUENCE LISTING

A computer readable XML file entitled "GWPCTP20221100780", that was created on Dec. 28, 2022, with a file size of 27, 731 bytes, contains the sequence listing for this application, has been filed with this application, and is hereby incorporated by reference in its entirety.

TECHNICAL FIELD

The invention relates to the use of gene encoding gibberellin 3β-hydroxylase of *Glycine max*, GmGA3ox1, which belongs to the field of genetic engineering.

BACKGROUND

*Glycine max*, dicotyledon, originated in China, is an important oil and food crop, which can provide abundant protein and sufficient oil for humans and animals, and has important economic value. *G. max* plays an important role in the development of the national economy and the production of international oil-bearing crops. As an important crop, the yield of *G. max* has always been the focus of attention. One of the primary goals of breeders is to cultivate high-yield and high-quality *G. max* varieties. The components of *G. max* yield can be analyzed from two aspects. One is that the yield is composed of biomass and harvest index, and the other is that it is composed of the number of plants per unit area, pod number per plant, seed number per pod, and 100-seed weight. *G. max* yield-related traits are complex quantitative traits controlled by multiple genes, and their performed traits are results of the interaction of genotype and environment. There are many factors affecting *G. max* yield, including growth morphological traits, photosynthetic physiological traits and yield components. Among them, the yield components of *G. max* include 100-seed weight, pod number per plant, seed number per plant, yield per plant, etc.

Gibberellin (GA) is a plant hormone that plays an important role in plant growth and development. Many studies have reported that GA is involved in regulating seed germination, leaf expansion, flowering and fruit development, as well as regulating environmental signals such as the duration of day. At the cellular level, GA also stimulates cell elongation and cell division. In addition, analysis of the currently cloned crop yield and yield-related trait genes function show that multiple yield-related genes are mainly related to GA synthesis or its regulatory pathways. GmGA3ox1 is a kind of gibberellin 3β-hydroxylase (GA3ox) of *G. max*. In plants, GA3ox is a key rate-limiting enzyme in the GA synthesis pathway, responsible for the synthesis of bioactive gibberellin, which is a key factor in regulating the synthesis of active GA. However, the function of GA3ox gene in *G. max* has not been reported.

SUMMARY

The purpose of the present disclosure is to disclose the use of gibberellin 3β-hydroxylase gene of *G. max*, GmGA3ox1, in genetic engineering to improve seed weight. Tissue expression and GUS staining analysis show that GmGA3ox1 is mainly expressed in *G. max* leaves and stems, and almost not expressed in other tissues. The expression level of GmGA3ox1 gene is positively correlated with *G. max* seed weight. In addition, subcellular localization analysis shows that GmGA3ox1 is localized in cell membrane and cytoplasmic matrix. The gene can be introduced into *Arabidopsis thaliana* and *G. max* as a target gene to increase the seed weight of transgenic *A. thaliana* and transgenic *G. max*.

The purpose of the present disclosure can be realized by the following technical scheme:

The use of gibberellin 3β-hydroxylase gene of *G. max*, GmGA3ox1, set forth in SEQ ID NO: 1 in genetic engineering of *A. thaliana* and *G. max* to improve seed weight. The nucleotide sequence set forth in SEQ ID NO: 1 is:

```
atgccttctc tctccgaagc ctttagaggt caccccgtgt accttcatca caaacactcc    60
gacttcaact cacttcaaga actccctgac tcttactctt ggacacaacc ccatgatcac   120
catctcccaa attacccttc caacaataag accaagatct ttgtccccgt aatcgatttg   180
aaccacccaa atgctccaaa cctcataggc catgcatgca aaacatgggg tgtgttccaa   240
gtggtgaacc atgacatccc catgagcctc ttcagtgaca ttcagagggc tagtcttgcg   300
ttattctccc ttccccttca ccagaagctc aaagcagctc gctcccccga cggcgtctcc   360
ggctatggcc gcgctcgcat ctcctccttc ttccccaagc tcatgtggtc tgagtgcttc   420
acaattctcg attcccctct tgatcttttc ctcaaactct ggccacaaga ctatgctaaa   480
tactgtgata ttgtcgtgga atatgaagca gccatgaaaa agctagcagc gaaattaatg   540
tgcctcatgt tggcttccct tggaattaca aaggaagaca ctaaatgggc tgggccaaaa   600
ggagaattca atggggcttg tgcggccttg cacttgaatt cttacccgag ttgcccggat   660
ccggatcgag ccatgggtct ggccgcacac accgactcca ctctcctcac aatcctacac   720
```

-continued

```
caaaacaatg tcaatgggct tcaagttctc aaggaaggag aagggtgggt ggcagtgccg    780
ccgcttcacg gagggctcgt gattaacgtt ggcgatctgc tccacatttt gtcaaacggg    840
ttgtacccga gtgtgctcca tcgggttcgg gtgaaccgaa cccaacagcg gttctcggtt    900
gcttatctat atgggccccc agcaaacgtc caaatcagtc cacatgtcaa gttggtgggc    960
ccaacaaggc ccgctcttta tcgaccagtg acttggaacg agtaccttgg caccaaagca   1020
aaccttttta ataaggctct ttcagcggtt aggctttctg cgtctattaa cggtttgttt   1080
gatataaacg aggatcagaa taacgacttt caagtgggct tcaatctaga tatttag.    1137
```

In *A. thaliana*, overexpression of GmGA3ox1 may complement the low seed weight phenotype of atga3ox1 mutant. In *G. max*, overexpression of the excellent haplotype of the GmGA3ox1 gene may significantly improve the seed weight of *G. max*.

Beneficial Effects

It is found that the GmGA3ox1 gene of *G. max* positively regulates the seed weight of transgenic *A. thaliana*. Through expression analysis, it is proved that GmGA3ox1 is mainly expressed in *G. max* leaves and stems, and positively correlated with *G. max* seed weight. Subcellular localization analysis shows that GmGA3ox1 is a membrane and cytoplasmic matrix localization protein. Through overexpression of GmGA3ox1, it is found that the gene positively regulated the seed weight of transgenic *Arabidopsis*. It can be seen that GmGA3ox1 is capable of being used as a target for regulating *G. max* seed weight for *G. max* yield improvement.

BRIEF DESCRIPTION OF THE DRAWINGS

FIGS. 4A-C depict GUS staining of GmGA3ox1 transgenic *A. thaliana*, N=3; (4A) GUS staining of GmGA3ox1$_{pro}$ (−1957): GUS transgenic *A. thaliana*; (4B) GUS staining of GmGA3ox1$_{pro}$ (−1005): GUS transgenic *A. thaliana*; (4C) GmGA3ox1$_{pro}$ (−487): GUS transgenic *A. thaliana*.

FIG. 5 depicts subcellular localization analysis of GmGA3ox1 protein. GFP: GFP fluorescence; Light: bright field; Merge: fusion protein; 35S: GFP: unloading control; 35S: GmGA3ox1-GFP: GFP-tagged GmGA3ox1 protein; scale: 20 μm.

DETAILED DESCRIPTION OF THE EMBODIMENTS

The present disclosure is further described below in combination with drawings and Examples.

The methods used in the following Examples are conventional methods unless otherwise specified.

Example 1

1) Cloning of Gibberellin 3β-Hydroxylase Gene of *G. max*, GmGA3ox1

The leaves of *G. max* variety, Nannong 1138-2, were taken and ground with a mortar, then added to a 1.5 mL EP tube containing lysis buffer. After full oscillation, the obtained mixture were transferred to a 1.5 mL EP tube to extract total RNA (Total RNA Kit, Tiangen, Beijing, China). The quality of total RNA was identified by Formaldehyde denatured gel electrophoresis, and the content of RNA was determined by spectrophotometer. The first strand of cDNA was obtained by using the total RNA as a template for reverse transcription according to the instructions of the reverse transcription kit (TaKaRa Primer Script TM RT reagent kit, Japan) provided by TaKaRa company in Japan, and amplified by PCR. The PCR procedure was as follows: pre-denaturation at 95° C. for 3 min, 35 cycles of denaturation at 95° C. for 15 sec, annealing at 60° C. for 15 sec, extension at 72° C. for 90 sec; at last holding at 72° C. for 5 min, followed by keeping in constant temperature of 12° C., then the cDNA of Nannong 1138-2 was obtained.

Figure 1:
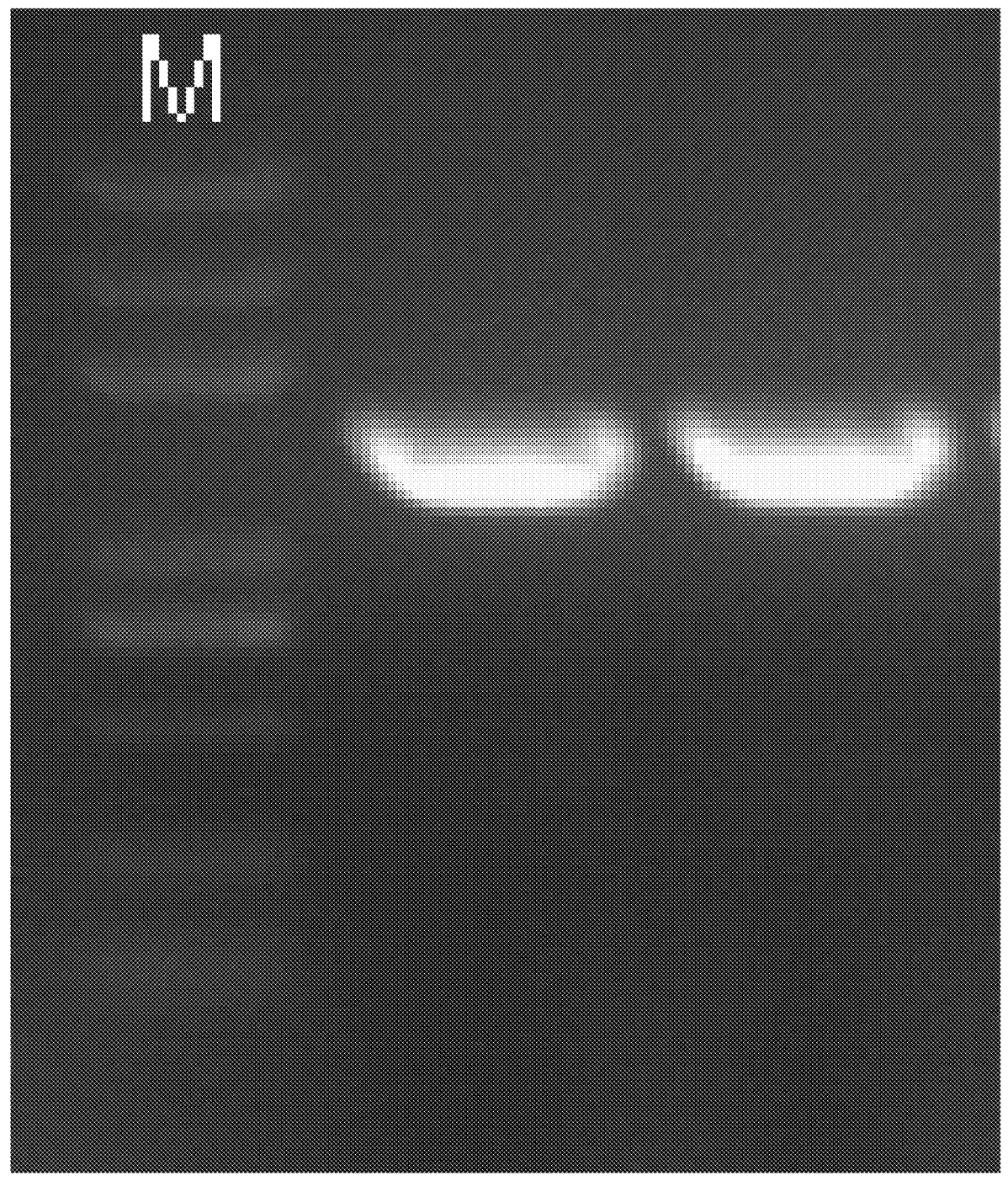
FIG. 1 depicts Agarose gel electrophogram of cloning GmGA3ox1 by PCR. Target fragment size is 1137 bp, Marker: DL2000Plus.

The gene corresponding to GmGA3ox1 (Glyma.07g033800, GeneID: 100795921) was found from NCBI database and Phytozome v12 *G. max* database. Specific primers were designed according to the nucleotide sequence provided by the database. The primer sequences were set forth in SEQ ID NO: 3 (atgcettete tetccgaagc ct) and SEQ ID NO: 4 (ctaaatatct agattgaag). Genes in coding sequence (CDS) of *G. max* variety Nannong 1138-2 was amplified. After PCR cloning, the obtained PCR products were purified, ligated and transformed. The positive clones were picked and sequenced. After sequencing, the CDS sequence of GmGA3ox1 gene of *G. max* with a complete coding region of 1137 bp was obtained, in which the coding sequence is set forth in SEQ ID NO: 1, with a size of 1137 bp (FIG. 1) (nucleotide sequence (SEQ ID NO: 1) and amino acid sequence (SEQ ID NO:2)).

```
The amino acid sequence set forth
in SEQ ID NO: 2 is:
MPSLSEAFRGHPVYLHHKHSDFNSLQELPDSYSWTQ

PHDHHLPNYPSNNKTKIFVPVIDLNHPNAPNLIGH

ACKTWGVFQVVNHDIPMSLFSDIQRASLALFSLPL

HQKLKAARSPDGVSGYGRARISSFFPKLMWSECFT

ILDSPLDLFLKLWPQDYAKYCDIVVEYEAAMKKLA

AKLMCLMLASLGITKEDTKWAGPKGEFNGACAALH

LNSYPSCPDPDRAMGLAAHTDSTLLTILHQNNVNG

LQVLKEGEGWVAVPPLHGGLVINVGDLLHILSNGL

YPSVLHRVRVNRTQQRFSVAYLYGPPANVQISPHV

KLVGPTRPALYRPVTWNEYLGTKANLFNKALSAVR

LSASINGLFDINEDQNNDFQVGFNLDI.
```

2) Tissue Expression Analysis of GmGA3ox1

In order to identify the expression level of GmGA3ox1 in different tissues, the roots, stems, leaves, flowers, pods and seeds of *G. max* variety Nannong 1138-2 at different developmental stages were collected: roots, stems and leaves were in stage V4; mature flowers were in stage R2; and seeds and pods were collected 15 days after flowering. The samples were frozen in liquid nitrogen and stored at −80° C. The extraction of total RNA was the same as step 1). The total RNA obtained from the above tissues was used as a template to reverse into cDNA. The fluorescent quantitative primer sequences of GmGA3ox1 were set forth in SEQ ID NO: 5 (agtccacatg tcaagttggtgg) and SEQ ID NO: 6 (cggttaggct ttctgcgtcta). The expression level of GmGA3ox1 gene in different tissues was detected with reference gene Tubulin in *G. max* as the internal reference. The primer sequences set forth in SEQ ID NO: 7 (cctcgttcga attcgcttttg) and SEQ ID NO: 8 (caactgtctt gtcacttggc at) were used for real-time fluorescence quantitative PCR (Real-time RT-PCR).

Figure 2:
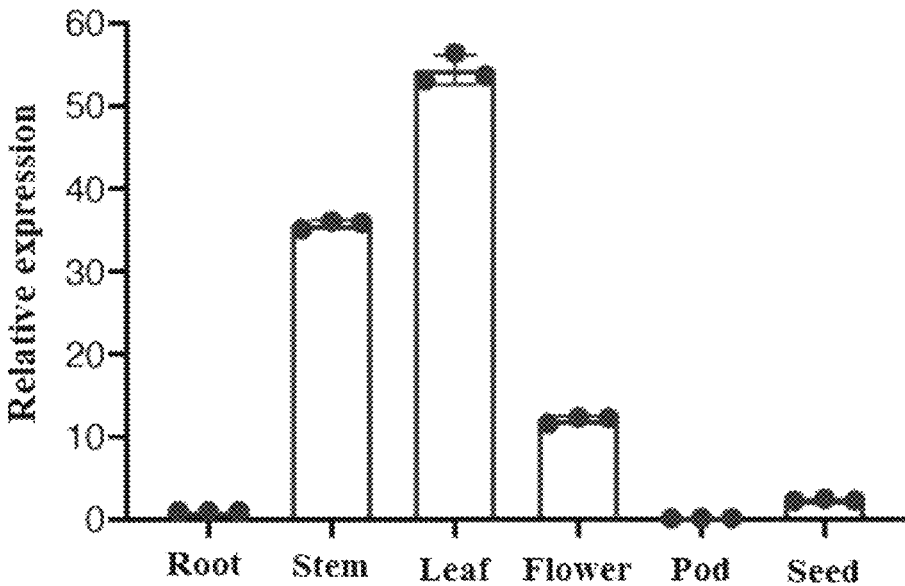
FIG. 2 depicts tissue expression pattern of GmGA3ox1, N=3.

GmGA3ox1 was mainly expressed in leaves and stems of *G. max*, and the expression level of which was low in roots, stems, flowers, pods and seeds (FIG. 2).

3) Correlation Analysis Between Expression Level of GmGA3ox1 and Seed Weight

39 *G. max* materials with different seed weights were selected and planted in greenhouse. The top three leaves of each *G. max* material were collected at stage V4, and the samples were frozen in liquid nitrogen and stored at −80° C. The extraction of total RNA was the same as step 1). The total RNA obtained from the above tissues was used as a template to reverse into cDNA. The expression level of GmGA3ox1 gene in each *G. max* material was detected by real-time fluorescence quantitative PCR (Real-time RT-PCR) with Tubulin as the reference gene. The primer sequences were set forth in SEQ ID NO:7 and SEQ ID NO: 8. The correlation between GmGA3ox1 expression level and seed weight was calculated by SPSS 20.0 software.

Figure 3:
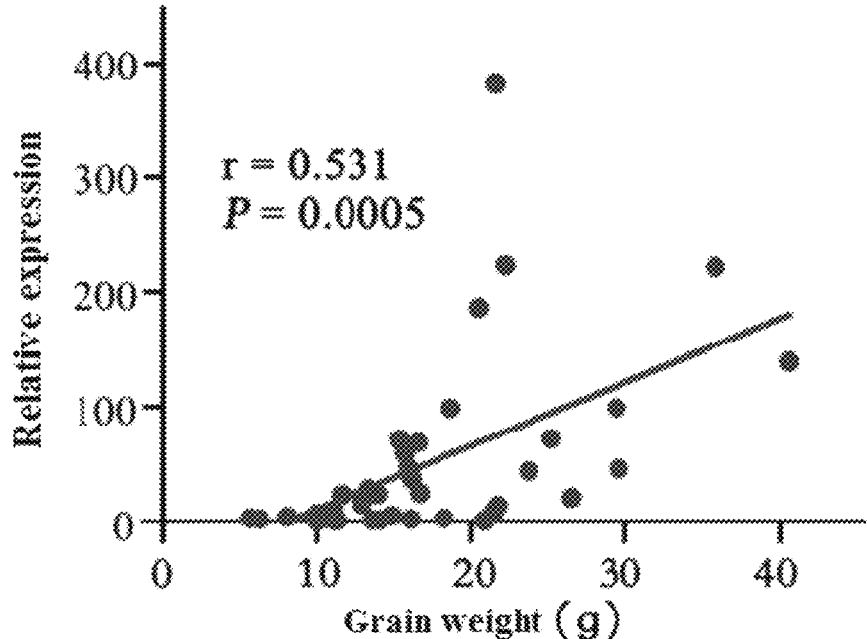
FIG. 3 depicts the expression level of GmGA3ox1 is positively correlated with *G. max* seed weight.
Figure 6A:
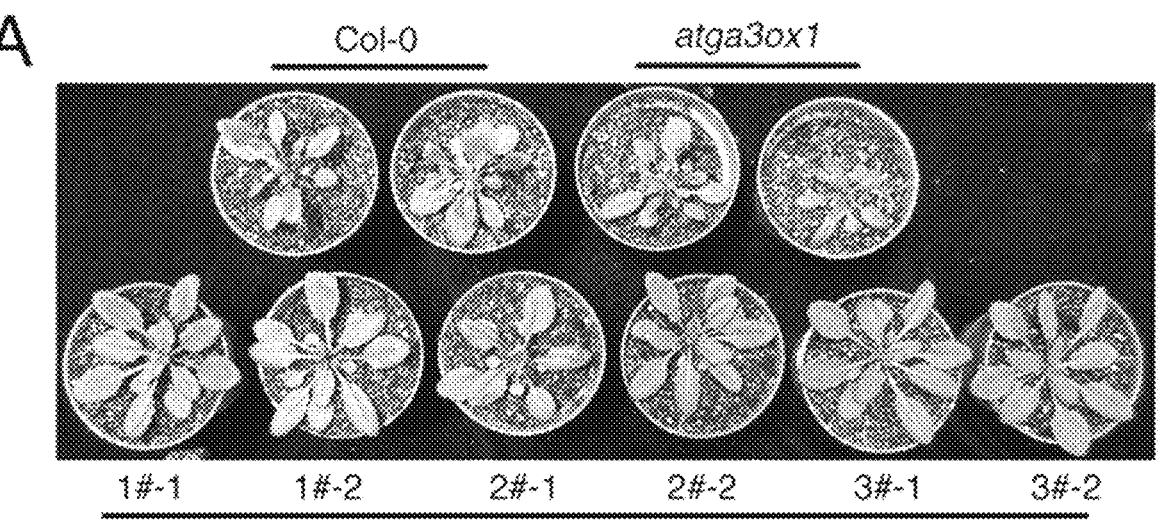
FIGS. 6A-D depict overexpression of GmGA3ox1 in atga3ox1 mutant improves the seed weight of *A. thaliana*. (6A) The rosette leaf phenotypes of 4-week-old *A. thaliana* wild type (Col-0), atga3ox1 mutant and three 35S: GmGA3ox1/atga3ox1 transgenic lines; (6B) Mature plant phenotypes of 7-week-old Col-0, atga3ox1 mutants and three 35S: GmGA3ox1/atga3ox1 transgenic lines. (6C) Seed phenotypes of Col-0, atga3ox1 mutant and three 35S: GmGA3ox1/atga3ox1 transgenic lines; scale=1 mm; (6D) Comparison of 1000-seed weight between atga3ox1 mutant and three 35S: GmGA3ox1/atga3ox1 transgenic lines, N=9; the error bar represents ±SEM. Statistical analysis is performed using a two-tailed t test, : P<0.01; *: P<0.001.
Figure 6B:
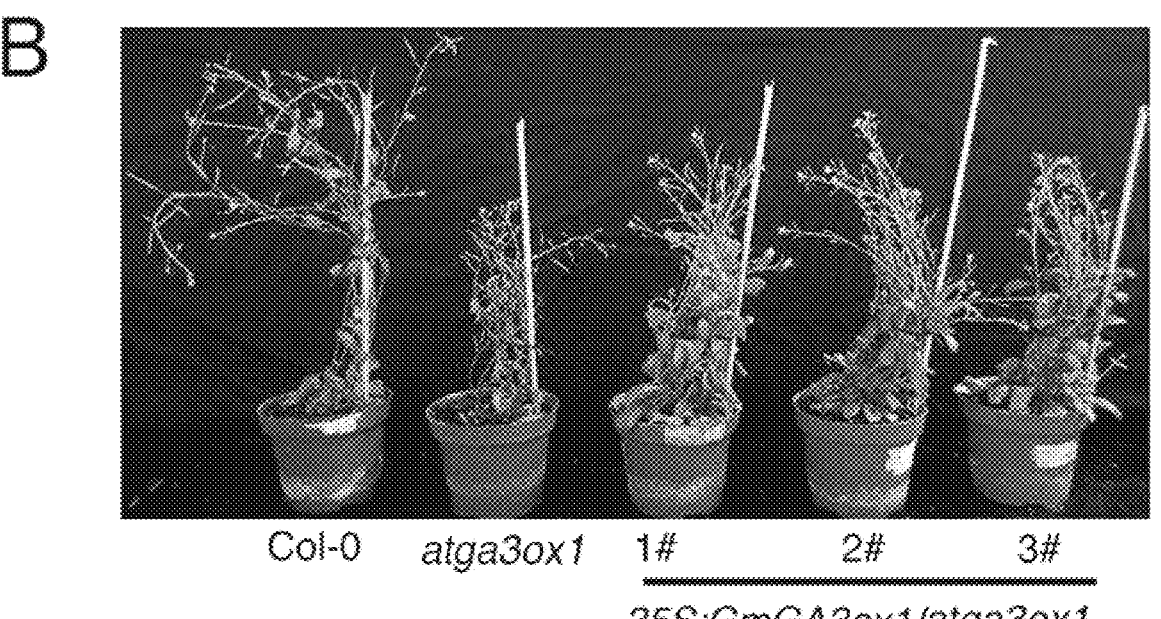
Figure 6C:
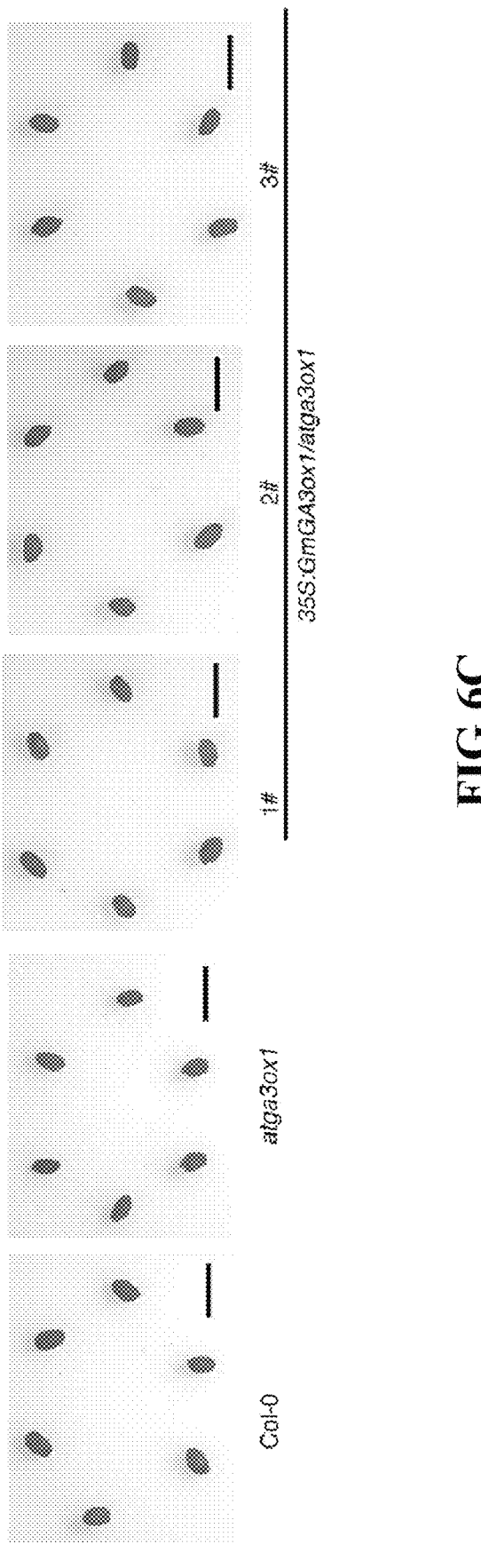
Figure 6D:
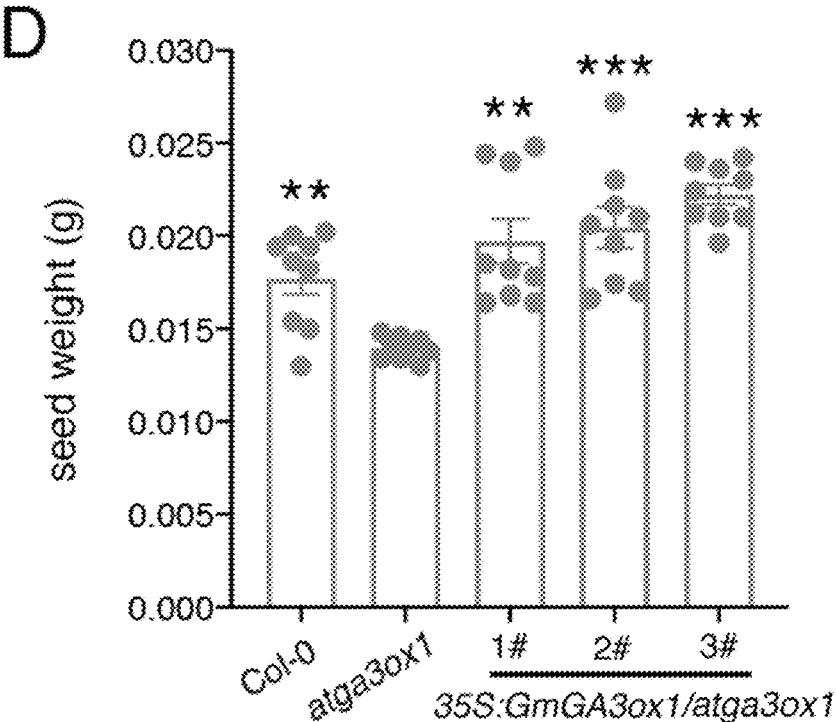

The correlation coefficient r between GmGA3ox1 expression level and seed weight was 0.531, and the P value was 0.0005. The results showed that the expression level of GmGA3ox1 gene was positively correlated with seed weight (FIG. 3).

Example 2

1) Cloning of Promoter Sequence of Gibberellin 3β-Hydroxylase Gene of *G. max*, GmGA3ox1

Leaf DNA of *G. max* Nannong 1138-2 was used as template for PCR amplification. The primer sequences were set forth in SEQ ID NO: 9 (cagctatgac catgattact cacatcgata aacgaggttt g), SEQ ID NO: 10 (agtgccaagc ttggctgcag attgtgttga atgcttcgg), SEQ ID NO: 11 (cagctatgac catgattact cacgatccca acattcgtg), SEQ ID NO: 12 (agtgccaagc ttggctgcag attgtgttga atgcttcgg), SEQ ID NO: 13 (cagctatgac catgattacc acctagtgag agagaaagaa gg) and SEQ NO: 14 (agtgccaagc ttggctgcag attgtgttga atgcttcgg). The PCR procedure was as follows: pre-denaturation at 95° C. for 3 min; 35 cycles of denaturation at 95° C. for 15 sec, annealing at 60° C. for 15 sec, extension at 72° C. for 90 sec; and at last holding at 72° C. for 5 min, followed by keeping in constant temperature of 4° C. After sequencing, GmGA3ox1 gene promoter sequences with length of 1957 bp, 1005 bp and 487 bp were obtained.

2) Construction of GUS Staining Vector

The sequences of promoters with different lengths of the three GmGA3ox1 genes were inserted into pCAMBIA1381Z vector, and then the obtained constructed vector was transferred into *Agrobacterium tumefaciens* strain EHA105 by freeze-thaw method.

3) GUS Staining of GmGA3ox1 Transgenic *A. thaliana*

The *A. thaliana* was transformed by the floral-dip method. The flower buds of *A. thaliana* were immersed in bacteria solution of the *A. tumefaciens* strain EHA105 containing GmGA3ox1$_{pro}$ (−1957): GUS, GmGA3ox1$_{pro}$ (−1005): GUS and GmGA3ox1$_{pro}$ (−487): GUS, respectively, and infected for 30 sec to 1 min. The plants were wrapped with preservative film or fresh-keeping bag to keep the humidity and cultured in dark for 24 h. After that, it could be transformed again after a new batch of inflorescence grew out, depending on the growth status of the plants. *A. thaliana* was put under normal conditions to continue growing and seeds of which were harvested. The roots, stems, leaves, flowers, pods and seeds of three homozygous T3 generation GmGA3ox1$_{pro}$ (−1957): GUS, GmGA3ox1$_{pro}$ (−1005): GUS and GmGA3ox1$_{pro}$ (−487): GUS transgenic *A. thaliana* lines were selected for GUS staining. The kit used for staining was from Beijing Solarbio Science and Technology Co., Ltd., with Item No. of G3060. In order to detect whether the transgenic *A. thaliana* is positive. The extracted DNA fragments were detected by PCR using specific primers set forth in SEQ ID NO: 9, SEQ ID NO: 10, SEQ ID NO: 11, SEQ ID NO: 12, SEQ ID NO: 13 and SEQ ID NO: 14. The PCR detection gel electropherogram was shown in FIG. 8.

Figures 4A, 4B, 4C, 5:
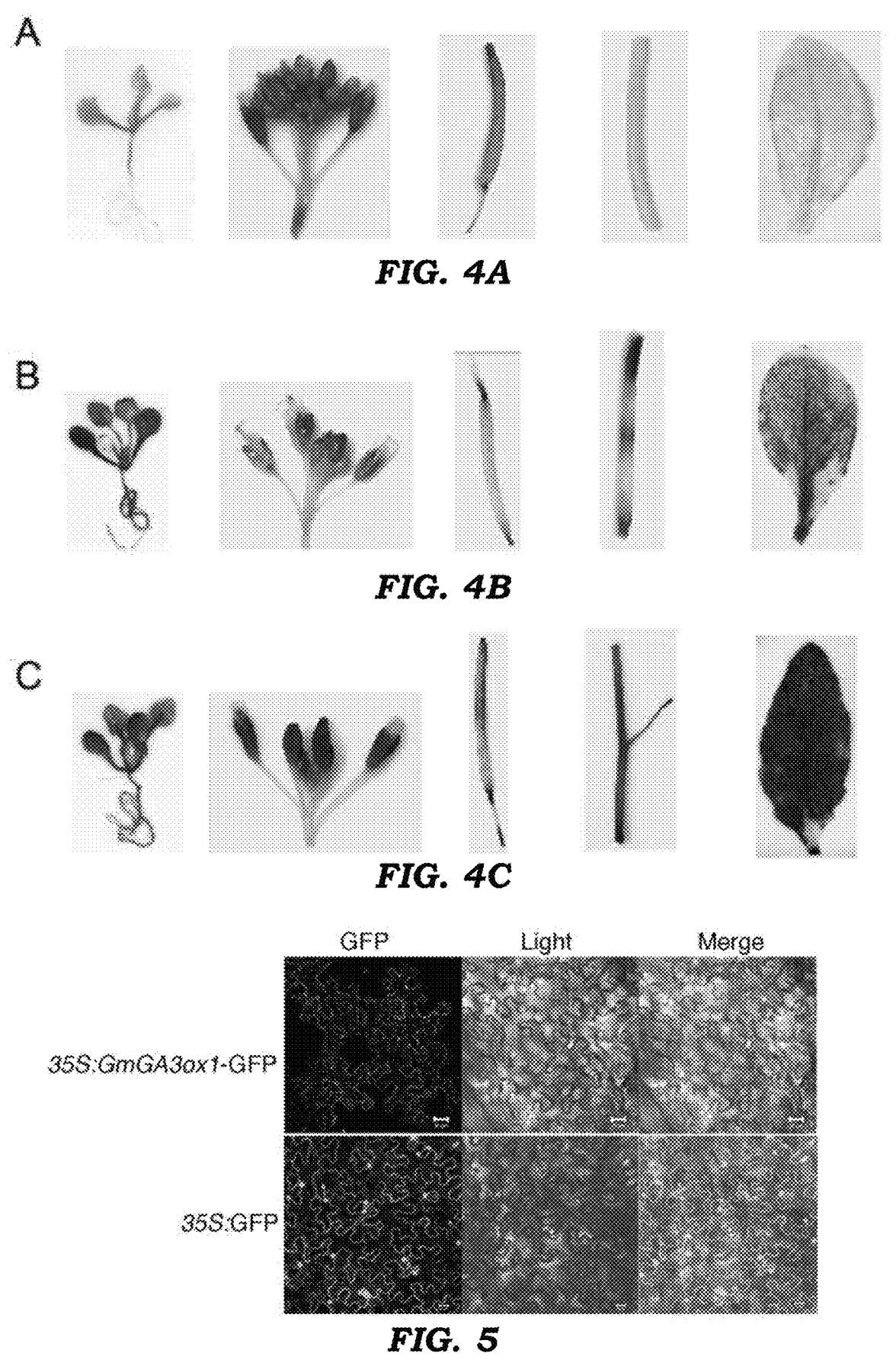

GUS staining results showed that the three types of GmGA3ox1 gene promoters all had high activity, and the tissues with the highest activity of these three types of promoters were located in leaves, followed by stems, flowers, seeds, pods and roots (FIGS. 4A-C).

Example 3

1) Cloning of Gibberellin 3β-Hydroxylase Gene of *G. max*, GmGA3ox1

The first strand of cDNA was synthesized by using the total RNA of *G. max* variety Nannong 1138-2 leaves as a template for reverse transcription, and then amplified by PCR. The primer sequences were set forth in SEQ ID NO: 15 (cctctagaat gccttcte tecgaagcct) and SEQ ID NO: 16 (ccgctcgaga atatctagat tgaag). The PCR procedure was as follows: pre-denaturation at 95° C. for 3 min; 35 cycles of denaturation at 95° C. for 15 sec, annealing at 60° C. for 15 sec, extension at 72° C. for 90 sec; at last holding at 72° C. for 5 min, followed by keeping in constant temperature of 4° C. After sequencing, the CDS sequence of GmGA3ox1 gene of *G. max* without stop codon was obtained.

2) Construction of Subcellular Localization Vector

The CDS sequence of GmGA3ox1 gene of *G. max* without stop codon was inserted into pFGC5941 expression vector containing GFP tag. The pFGC5941 vector had a 35S promoter, which could strongly induce the expression of the target gene GmGA3ox1 in the receptor. Then the constructed vector was transferred into *A. tumefaciens* strain EHA105 by freeze-thaw method. At the same time, the unloading pFGC5941 vector was also transformed into EHA105 as a control.

3) Subcellular Localization of GmGA3ox1

The bacterial solution containing 35S: GmGA3ox1-GFP and 35S: GFP were injected into the leaves of *Nicotiana benthamiana* with the size of 7-8 weeks, respectively. After 36-48 hours of cultivation, the localization of the reporter gene GFP was observed by Leica TCS SP2 laser confocal microscopy. The GFP signal showed that the GmGA3ox1-GFP fusion protein was localized to the cell membrane and cytoplasmic matrix, while the unloading vector was localized to the entire tobacco cells (FIG. 5).

Example 4: Use of Gene GmGA3ox1 in Genetic Engineering

1) Cloning of Gibberellin 3β-Hydroxylase Gene of *G. max*, GmGA3ox1

The first strand of cDNA was synthesized by using total RNA of *G. max* variety Nannong 1138-2 leaves as a template for reverse transcription, and then amplified by PCR. The primer sequences were set forth in SEQ ID NO: 17 (gtcgacgta tegataagct tatgccttct ctctctccgaag cc), SEQ ID NO: 18 (cgctctagaaa ctagtggatc cctaaatatc tagattgaag cccac). The PCR procedure was as follows: pre-denaturation at 95° C. for 3 min; 35 cycles of denaturation at 95° C. for 15 sec, annealing at 60° C. for 15 sec, extension at 72° C. for 90 sec; and at last holding at 72° C. for 5 min, followed by keeping in constant temperature of 4° C. After sequencing, the CDS sequence of GmGA3ox1 gene of *G. max* with a complete coding region length of 1137 bp was obtained. In addition, the first strand of cDNA was synthesized by using the total RNA of the leaves of the local variety of *G. max* Jurong Flat Green Bean as a template for reverse transcription, and then amplified by PCR. The primer sequences were set forth in SEQ ID NO: 19 (ggatatgttg aaactttcct ttgc) and SEQ ID NO: 20 (atgcatgatc aatcatttac). The PCR procedure was as follows: pre-denaturation at 95° C. for 3 mins; 35 cycles of denaturation at 95° C. for 15 sec, annealing at 60° C. for 15 sec, extension at 72° C. for 120 sec; and at last holding at 72° C. for 5 min, followed by keeping in constant temperature of 4° C. After sequencing, GmGA3ox1 genome sequence of *G. max* with length of 4187 bp was obtained.

2) Construction of Plant Expression Vector

When constructing overexpression vector for transforming *A. thaliana*, the CDS sequence of GmGA3ox1 gene amplified from Nannong 1138-2 leaves was inserted into pBI121 expression vector to obtain pBI121-GmGA3ox1 plant overexpression vector. The plant transformation vector pBI121 contained a 35S strong promoter, which could strongly induce the expression of the target gene GimGA3ox1 in the receptor. Then the vector was transferred into *A. tumefaciens* strain EHA105 by freeze-thaw method.

When constructing the overexpression vector of *G. max*, the GmGA3ox1 genomic sequence with length of 4187 bp was amplified from the *G. max* Jurong Flat Green Bean. The 4187 bp fragment included 1554 bp promoter and 5'UTR region, 1899 bp intron and exon region and 539 bp 3'UTR region. The 4187 bp fragment was ligated into pCAMBIA3301 vector without CaMV 35S promoter to obtain pCAMBIA3301-GmGA3ox1 plant overexpression vector. The obtained vector was transformed into *A. tumefaciens* strain EHA105.

3) Obtaining Transgenic *A. thaliana* Plants

The *A. thaliana* was transformed by the floral-dip method. The flower buds of atga3ox1 *A. thaliana* mutant were immersed in bacteria solution of *A. tumefaciens* strain EHA105 containing pBI121-GmGA3ox1 in Step 2) and infected for 30 sec to 1 min. The plants were wrapped with preservative film or fresh-keeping bag to keep the humidity and cultured in dark for 24 h. After that, it could be transformed again after a new batch of inflorescence grew out, depending on the growth status of the plants. *A. thaliana* was put under normal conditions to continue growing and seeds of which were harvested. Three homozygous T 3 generation 35S: GmGA3ox1/atga3ox1 transgenic *A. thaliana* lines were selected to investigate the seed weight phenotype (FIGS. 6A-D). The extracted DNA fragments were detected by PCR using specific primers (SEQ ID NO: 21: atgccttctc tctccgaagc ct, SEQ ID NO: 22: aagaceggca acaggattca) to detect whether they were atga3ox1 mutants and whether they were overexpressed GmGA3ox1 transgenic *A. thaliana*. The PCR detection gel electropherogram was shown in FIGS. 8A-F.

Seeds of Col-0, atga3ox1 mutant and three 35S: GmGA3ox1/atga3ox1 transgenic lines were harvested after maturation and dried in an oven at 37° C. for one week. After seed drying, the 1000-seed weight (N=3) of Col-0, atga3ox1 mutant and three 35S: GmGA3ox1/atga3ox1 transgenic lines were measured. The 1000-seed weight of Col-0 lines was significantly higher than that of atga3ox1 mutant plants (FIG. 6D), which proved that the mutation of AtGA3ox1 gene in *A. thaliana* could significantly reduce seed weight. In addition, the seed weights of three 35S: GmGA3ox1/ atga3ox1 transgenic lines were significantly higher than that of atga3ox1 mutant plants and slightly higher than that of Col-0 plants (FIG. 6D), which proved that overexpression of GmGA3ox1 gene in atga3ox1 mutant could improve seed weight.

4) Obtaining Transgenic Plants of *G. max*

The *G. max* cultivar Williams 82 was transformed by cotyledonary node transformation method. The leaf axil of the *G. max* seedlings grown for 5 to 6 days were wounded, and the pCAMBIA3301-GmGA3ox1 vectors obtained in step 2) were inoculated into the wounds of the leaf axil. After co-culture at 25° C. for 4-5 days, the *G. max* was washed with sterilized ultra-pure water and WISH-LIQUID respectively, placed in SIM medium without glufosinate ammonium, and cultured at 26° C. for 15 days to induce buds. After 15 days, the *G. max* was placed in SIM medium containing 6 mg/L glufosinate ammonium. Subculture was then performed on a 15-day cycle to gradually reduce the dose of glufosinate ammonium. When the buds of the explants grew to about 6 cm, the explants were transferred into the rooting medium and cultured for about 10 days to induce roots. They could be transplanted after the roots grew well. The extracted DNA fragments were detected by PCR using specific primers (SEQ ID NO: 23: agtccacatg tcaagttgt gg, SEQ ID NO: 24: ccggcaacag gattcaatct taa) to detect whether they were transgenic *G. max* overexpressing GmGA3ox1. The PCR detection gel electropherogram was shown in FIGS. 8A-F.

Figure 7A:
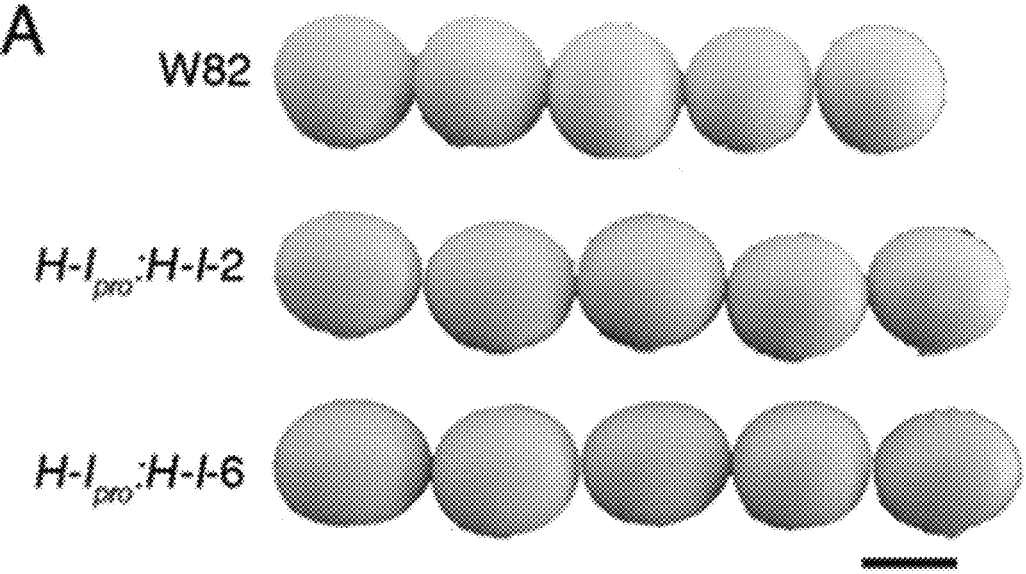
FIGS. 7A-G. The excellent haplotype with GmGA3ox1 overexpression improves the seed weight of *G. max*. (7A) Seed phenotypes of Williams 82 (W82) and two GmGA3ox1-OE transgenic lines; (7B) Schematic diagram of seed length, width, height of *G. max*; (7C) The relative expression level of GimGA3ox1 in W82 and two GmGA3ox1-OE transgenic lines, N=3; (7D) 100-seed weight of W82 and two GmGA3ox1-OE transgenic lines, N=10; (7E) Seed length of W82 and two GmGA3ox1-OE transgenic lines, N=10; (7F) Seed width of W82 and two GmGA3ox1-OE transgenic lines, N=10; (7G) Seed height of W82 and two GmGA3ox1-OE transgenic lines, N=10; the error bar represents ±SEM. Statistical analysis is performed using a two-tailed t test, : P<0.01; *: P<0.001; ns: not significant.
Figure 7B:
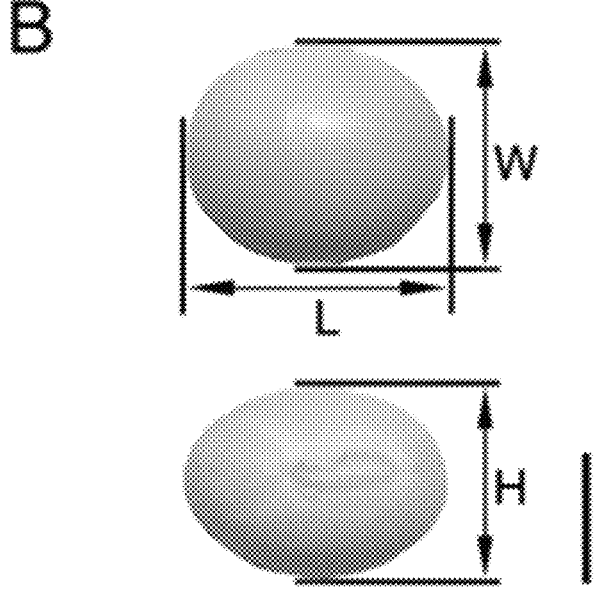
Figure 7C:
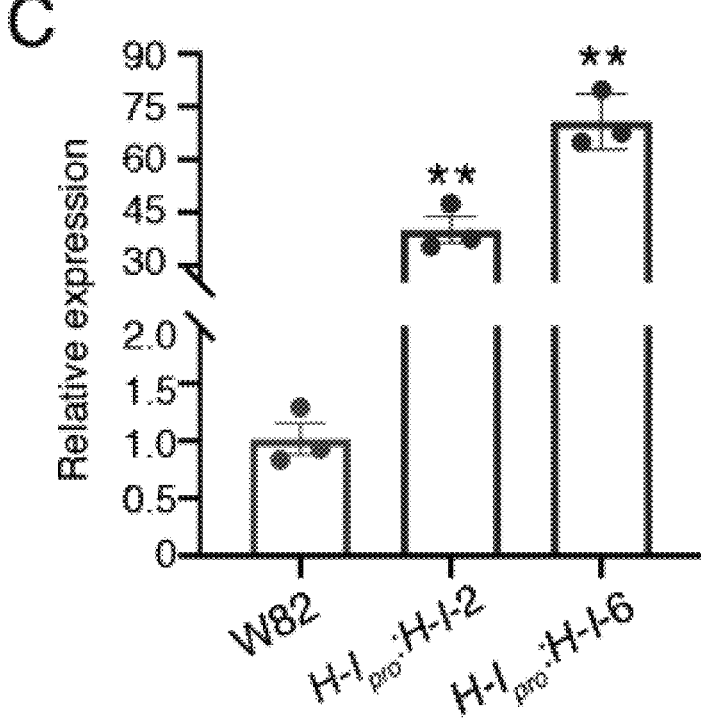
Figure 7D:
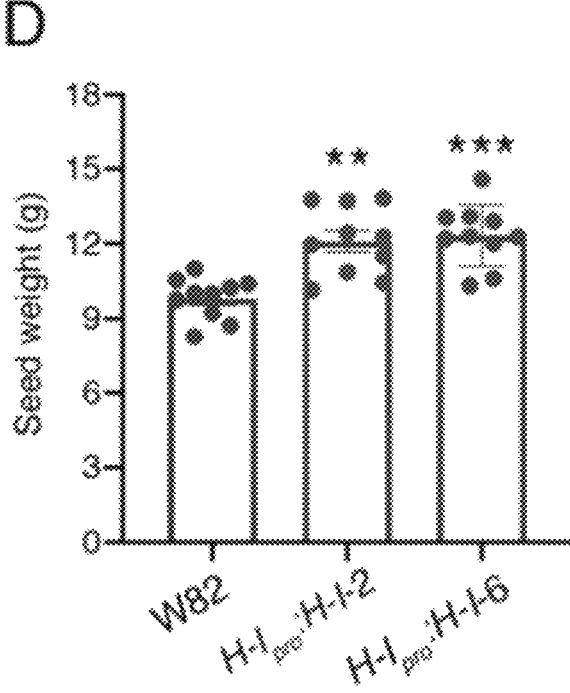
Figure 7E:
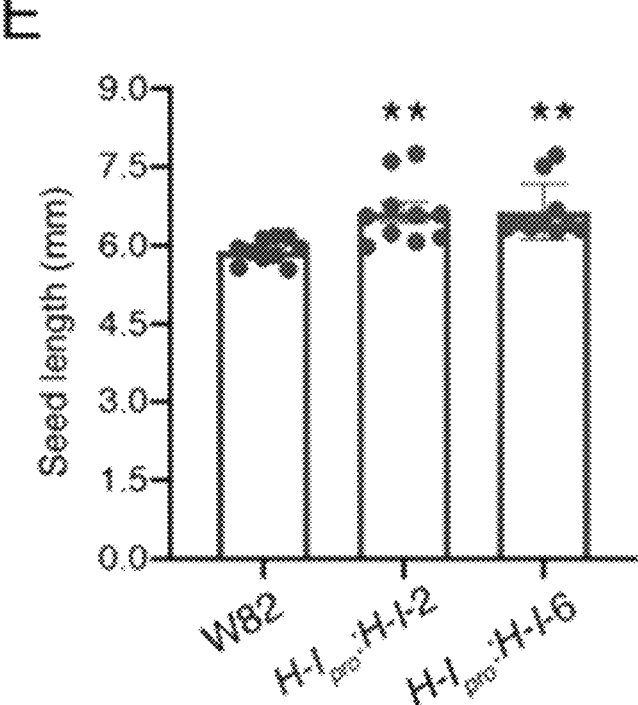
Figure 7F:
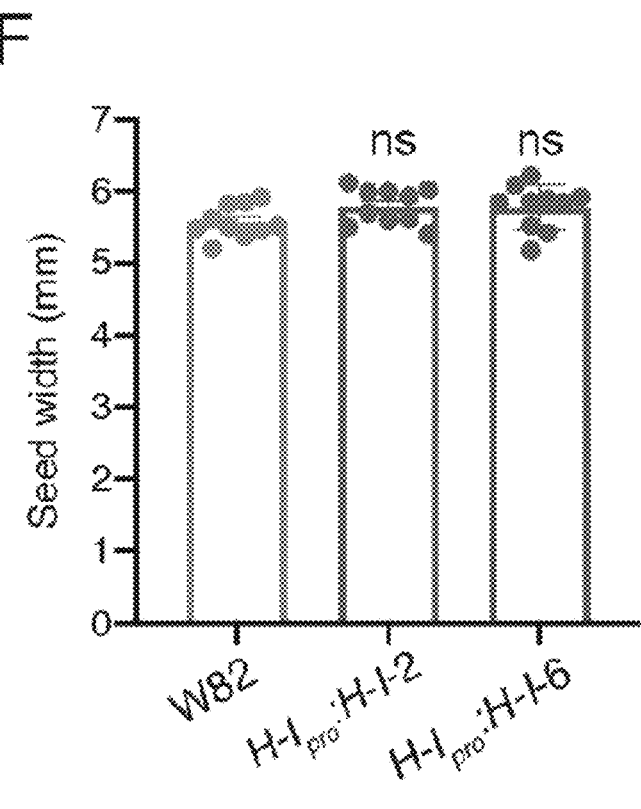
Figure 7G:
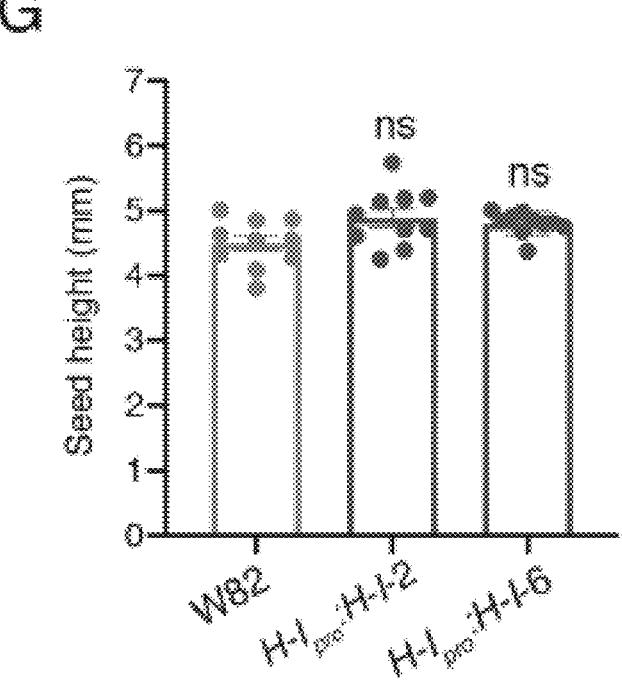
Figure 8A:
FIGS. 8A-F depict PCR detection of transgenic *A. thaliana* and *G. max*; (8A) Detection of GmGA3ox1$_{pro}$ (−1957): GUS transgenic *A. thaliana*, target fragment size of 1957 bp, M: Marker DL2000, P: positive plasmid, ck: *A. thaliana* wild type, 1-6: different GmGA3ox1$_{pro}$ (−1957): GUS transgenic plants, H$_2$O: blank control; (8B) Detection of GmGA3ox1$_{pro}$ (−1005): GUS transgenic *A. thaliana*, target fragment size of 1005 bp, M: Marker DL2000, P: positive plasmid, ck: *A. thaliana* wild type, 1-6: different GmGA3ox1$_{pro}$ (−1005): GUS transgenic plants, H$_2$O: blank control; (8C) Detection of GmGA3ox1$_{pro}$ (−487): GUS transgenic *A. thaliana*, target fragment size of 487 bp, M: Marker DL2000, P: positive plasmid, ck: *A. thaliana* wild type, 1-6: different GmGA3ox1$_{pro}$ (−487): GUS transgenic plants, H$_2$O: blank control; (8D) PCR detection of *A. thaliana* atga3ox1 mutant by setting a specific amplification time, and in the set time, a fragment with fragment size of 2000 bp cannot be amplified in atga3ox1 mutant, but can be amplified in the wild-type plant Col-0, M: Marker DL2000, Col-0: *A. thaliana* wild-type Col-0, atga3ox1: *A. thaliana* atga3ox1 mutant, H$_2$O: blank control; (8E) PCR detection of GmGA3ox1 transgenic *A. thaliana*, target fragment size of 1137 bp, M: Marker DL2000, Col-0: *A. thaliana* wild type Col-0, atga3ox1: *A. thaliana* atga3ox1 mutant, H$_2$O: blank control, 1-6: different 35S: GmGA3ox1/atga3ox1 transgenic plants; (8F) PCR detection of GmGA3ox1 transgenic *G. max*, target fragment size of 800 bp, M: Trans5K DNA Marker, P: positive plasmid, ck: wild type *G. max* W82, H$_2$O: blank control, 1-6: different GmGA3ox1 transgenic plants.
Figure 8B:
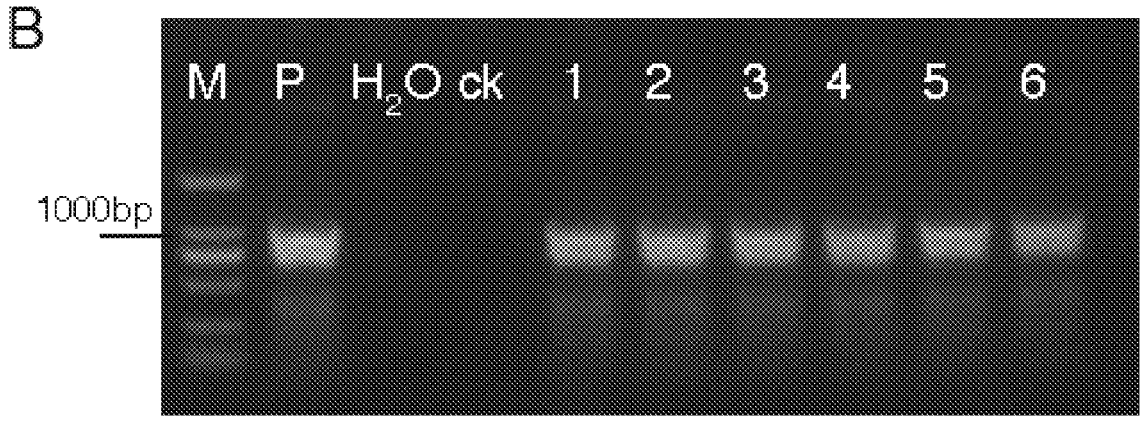
Figure 8C:
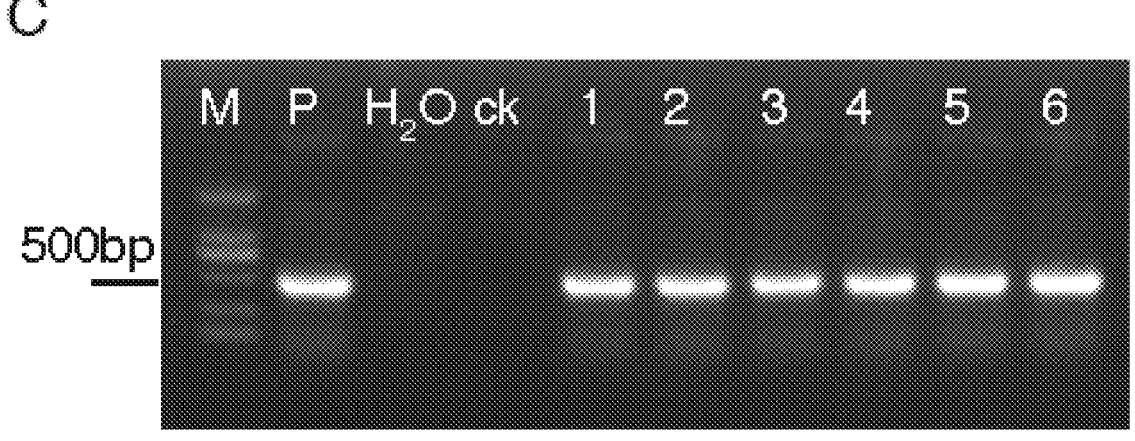
Figure 8D:
Figure 8E:
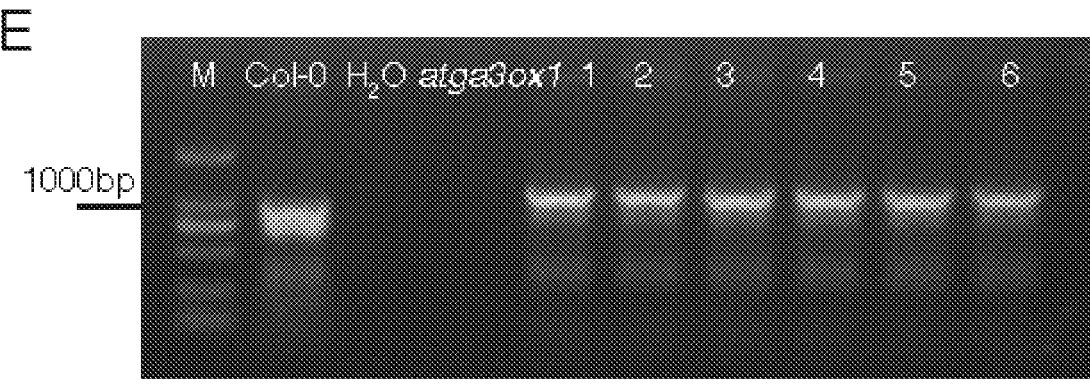
Figure 8F:
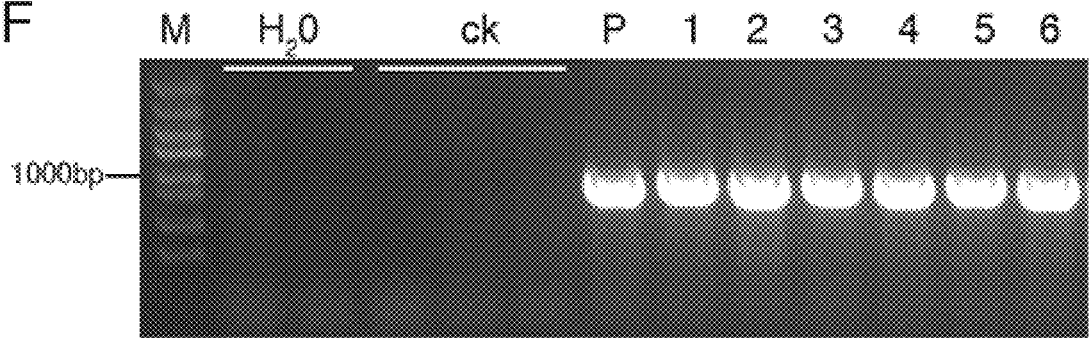

The obtained transgenic plants of *G. max* and their controls were sown in flowerpots and placed in a net room under natural conditions. After harvest, the seeds were dried in an oven at 37° C. for one week. After seed drying, 100-seed weight, seed length, width and height (N=10) of W82 and two GmGA3ox1 transgenic *G. max* lines were measured. The expression levels of GmGA3ox1 in the two transgenic *G. max* lines were significantly higher than that in the control W82 plants (FIG. 7C) (primers were SEQ ID NO: 23 and SEQ ID NO: 24), which proved that this promoter could effectively drive the expression of GmGA3ox1. In addition, the 100-seed weights and seed lengths of the two GmGA3ox1 transgenic *G. max* lines were significantly greater than those of W82 plants, and there was no significant difference in seed width and seed height between the two GmGA3ox1 transgenic *G. max* lines and W82 plants (FIGS. 7A, B, D-G), which proved that over-expression of the excellent haplotype gene of GmGA3ox1 could improve the seed weight and seed length of transgenic *G. max*.

The above description of Examples is intended to facilitate the convenience of ordinary persons skilled in the art to understand and use the present disclosure. It is clear that those familiar with the technology in the art can easily make various modifications to these Examples and apply the general principles described herein to other embodiments without creative labor. Therefore, the present disclosure is not limited to the above Examples. Improvements and modifications made by those skilled in the art according to the present disclosure are within the claimed scope of the present disclosure.

What is claimed is:

1. A method for genetic engineering of seed weight or length of *Glycine max, comprising using a sequence of Glycine max;* wherein the method for genetic engineering comprises: using DNA of leaves of Jurong Flat Green Bean as a template, amplifying the DNA using primers set forth in SEQ ID NO: 19 and SEQ ID NO: 20 to obtain a sequence of *Glycine max* with a length of 4187 bp, ligating the sequence of *Glycine max* into a pCAMBIA3301 vector without a CaMV 35S promoter to obtain a pCAMBIA3301-GmGA3ox1 plant overexpression vector, wherein a representative sample has been deposited under CGMCC deposit number 34555, transferring the pCAMBIA3301-GmGA3ox1 plant overexpression vector into *Agrobacterium tumefaciens* strain EHA105, and using the resulting EHA105 transformant to transform *Glycine max* cultivar Williams 82.

2. A method for improving the yield of *Glycine max*, comprising the following steps: overexpressing a protein of *Glycine max* or a gene encoding the protein of *Glycine max*, in *Glycine max;* wherein the overexpressing step comprises:

using DNA of leaves of Jurong Flat Green Bean as a template, amplifying the DNA using primers set forth in SEQ ID NO: 19 and SEQ ID NO: 20 to obtain a sequence of *Glycine max* with a length of 4187 bp, ligating the sequence of *Glycine max* into a pCAMBIA3301 vector without a CaMV 35S promoter to obtain a pCAMBIA3301-GmGA3ox1 plant overexpression vector, wherein a representative sample has been deposited under CGMCC deposit number 34555, transferring the pCAMBIA3301-GmGA3ox1 plant overexpression vector into *Agrobacterium tumefaciens* strain EHA105, and using the resulting EHA105 transformant to transform *Glycine max* cultivar Williams 82.

* * * * *